United States Patent
Janka et al.

(10) Patent No.: US 9,040,748 B2
(45) Date of Patent: May 26, 2015

(54) HYDROCARBOXYLATION OF AQUEOUS FORMALDEHYDE USING A DEHYDRATING RECYCLE STREAM TO DECREASE WATER CONCENTRATION

(75) Inventors: Mesfin Ejerssa Janka, Kingsport, TN (US); Scott Donald Barnicki, Kingsport, TN (US); Robert Thomas Hembre, Johnson City, TN (US); Kelley Margaret Moran, Kingsport, TN (US); Stephen Neal Falling, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 368 days.

(21) Appl. No.: 13/491,954

(22) Filed: Jun. 8, 2012

(65) Prior Publication Data

US 2013/0331605 A1 Dec. 12, 2013

(51) Int. Cl.
*C07C 51/12* (2006.01)
*C07C 27/04* (2006.01)
*C07C 29/149* (2006.01)

(52) U.S. Cl.
CPC .............. *C07C 51/12* (2013.01); *C07C 29/149* (2013.01)

(58) Field of Classification Search
CPC ............................. C07C 29/149; C07C 51/12
See application file for complete search history.

(56) References Cited

U.S. PATENT DOCUMENTS

| | | | |
|---|---|---|---|
| 2,152,852 A | 4/1939 | Loder | |
| 2,153,064 A | 4/1939 | Larson | |
| 2,158,107 A | 5/1939 | Carruthers et al. | |
| 2,211,624 A | 8/1940 | Loder et al. | |
| 2,211,625 A | 8/1940 | Loder | |
| 2,298,138 A | 10/1942 | Loder | |
| 2,443,482 A | 6/1948 | Shattuck | |
| 2,573,701 A | 11/1951 | Filachione et al. | |
| 2,686,797 A | 8/1954 | Bersworth et al. | |
| 3,333,924 A | 8/1967 | Hazen et al. | |
| 3,751,453 A | 8/1973 | Kurkov et al. | |
| 3,754,028 A | 8/1973 | Lapporte et al. | |
| 3,801,627 A | 4/1974 | Kurkov et al. | |
| 3,859,349 A | 1/1975 | Cody | |
| 3,911,003 A | 10/1975 | Suzuki | |
| 3,927,078 A | 12/1975 | Lapporte et al. | |
| 3,948,977 A | 4/1976 | Suzuki | |
| 3,948,986 A | 4/1976 | Suzuki | |
| 4,016,208 A | 4/1977 | Suzuki | |
| 4,052,452 A | 10/1977 | Scardigno et al. | |
| 4,087,470 A * | 5/1978 | Suzuki | 568/864 |
| 4,112,245 A | 9/1978 | Zehner et al. | |
| 4,128,575 A | 12/1978 | Leupold et al. | |
| 4,136,112 A | 1/1979 | Bakshi | |
| 4,140,866 A | 2/1979 | Nielsen | |
| 4,153,809 A | 5/1979 | Suzuki | |
| 4,228,305 A | 10/1980 | Suzuki | |
| 4,275,234 A | 6/1981 | Baniel et al. | |
| 4,291,007 A | 9/1981 | Baniel | |
| 4,308,397 A | 12/1981 | Suzuki | |
| 4,366,333 A | 12/1982 | Wilkes | |
| 4,409,395 A | 10/1983 | Miyazaki et al. | |
| 4,431,486 A * | 2/1984 | Balmat | 203/69 |
| 4,440,734 A | 4/1984 | Kougioumoutzakis | |
| 4,501,917 A | 2/1985 | Schmidt et al. | |
| 4,502,923 A | 3/1985 | Dyroff et al. | |
| 4,602,102 A | 7/1986 | Yeakey et al. | |
| 4,691,048 A | 9/1987 | Hughes et al. | |
| 4,824,997 A | 4/1989 | Macfarlane et al. | |
| 4,867,849 A | 9/1989 | Cova et al. | |
| 4,935,102 A | 6/1990 | Berg | |
| 4,966,658 A | 10/1990 | Berg | |
| 4,990,629 A | 2/1991 | Souma | |
| 5,026,927 A | 6/1991 | Andrews et al. | |
| 5,210,335 A | 5/1993 | Schuster et al. | |
| 5,214,219 A | 5/1993 | Casale et al. | |
| 5,217,582 A | 6/1993 | Heinsohn et al. | |
| 5,276,181 A | 1/1994 | Casale et al. | |
| 5,423,955 A | 6/1995 | Berg | |
| 5,455,372 A | 10/1995 | Hirai et al. | |
| 5,723,662 A | 3/1998 | Ebmeyer et al. | |
| 5,900,491 A | 5/1999 | Kurashima et al. | |
| 5,932,772 A | 8/1999 | Argyropoulos et al. | |
| 5,952,530 A | 9/1999 | Argyropoulos et al. | |
| 6,252,121 B1 | 6/2001 | Argyropoulos et al. | |
| 6,291,725 B1 | 9/2001 | Chopade et al. | |
| 6,294,700 B1 | 9/2001 | Kanel et al. | |

(Continued)

FOREIGN PATENT DOCUMENTS

| | | |
|---|---|---|
| DE | 3133353 C2 | 3/1983 |
| EP | 0 114 657 B1 | 3/1987 |

(Continued)

OTHER PUBLICATIONS

Notification of Transmittal of the International Search Report and the Written Opinion of the International Search Authority with Mail Date of Mar. 15, 2012 for International Application No. PCT/US2011/051490.

(Continued)

*Primary Examiner* — Paul A Zucker
(74) *Attorney, Agent, or Firm* — Jennifer R. Knight

(57) ABSTRACT

Disclosed is a process for the production and purification of glycolic acid or glycolic acid derivatives by the carbonylation of aqueous formaldehyde. The water in the hydrocarboxylation zone is reduced via reaction with the ester bonds in a recycle stream comprising glycolic acid oligomers and/or methyl glycolate oligomers.

17 Claims, No Drawings

(56) References Cited

U.S. PATENT DOCUMENTS

| | | | |
|---|---|---|---|
| 6,303,829 | B1 | 10/2001 | Kanel et al. |
| 6,307,108 | B1 | 10/2001 | Argyropoulos et al. |
| 6,307,109 | B1 | 10/2001 | Kanel et al. |
| 6,307,110 | B1 | 10/2001 | Argyropoulos et al. |
| 6,310,260 | B1 | 10/2001 | Argyropoulos et al. |
| 6,362,265 | B1 | 3/2002 | Wo et al. |
| 6,376,723 | B2 | 4/2002 | Drent et al. |
| 6,998,462 | B2 | 2/2006 | Duan et al. |
| 7,005,536 | B2 | 2/2006 | Hayashi et al. |
| 7,122,698 | B2 | 10/2006 | Yoshida et al. |
| 7,164,040 | B2 | 1/2007 | Kuroda et al. |
| 7,186,272 | B2 | 3/2007 | Heller |
| 7,223,885 | B2 | 5/2007 | Van Krieken |
| 7,439,391 | B2 | 10/2008 | Gallagher et al. |
| 7,615,671 | B2 | 11/2009 | Puckette et al. |
| 7,772,423 | B2 | 8/2010 | Celik et al. |
| 2005/0096481 | A1 | 5/2005 | Hildebrandt et al. |
| 2006/0079711 | A1 | 4/2006 | Hayashi et al. |
| 2007/0123739 | A1 | 5/2007 | Crabtree et al. |
| 2008/0275277 | A1 | 11/2008 | Kalagias |
| 2009/0143612 | A1 | 6/2009 | Puckette et al. |
| 2011/0144388 | A1 | 6/2011 | Sun et al. |
| 2011/0166383 | A1 | 7/2011 | Sun et al. |
| 2012/0046481 | A1 | 2/2012 | Barnicki et al. |
| 2012/0046500 | A1 | 2/2012 | Barnicki et al. |
| 2012/0078010 | A1 | 3/2012 | Barnicki et al. |

FOREIGN PATENT DOCUMENTS

| | | |
|---|---|---|
| EP | 0 676 239 A2 | 10/1995 |
| EP | 1 679 331 A1 | 7/2006 |
| GB | 508383 A | 6/1939 |
| GB | 1222008 A | 2/1971 |
| GB | 1499245 A | 1/1978 |
| GB | 2179337 A | 7/1986 |
| IL | 89044 A | 3/1993 |
| JP | 56100741 A | 8/1981 |
| JP | 56122321 A | 9/1981 |
| JP | 56131546 A | 10/1981 |
| JP | 56133237 A | 10/1981 |
| JP | 5746934 A | 3/1982 |
| JP | 57040442 A | 3/1982 |
| JP | 57102837 A | 6/1982 |
| JP | 57118533 A | 7/1982 |
| JP | 6228045 A | 8/1994 |
| JP | 1999147042 A | 6/1999 |
| JP | 2004131411 A | 4/2004 |
| JP | 2004182645 A | 7/2004 |
| SU | 1436453 A1 | 9/1996 |
| WO | WO 97/15543 A1 | 5/1997 |

OTHER PUBLICATIONS

Notification of Transmittal of the International Search Report and the Written Opinion of the International Search Authority with Mail Date of Nov. 28, 2011 for International Application No. PCT/US2011/047842.

Celik et al., "Synthesis of precursors to ethylene glycol from formaldehyde and methyl formate catalyzed by heteropoly acids", Journal of Molecular Catalysis A: Chemical 288, (2008), pp. 87-96.

Celik et al., "Vapor-phase carbonylation of dimethoxymethane of H-Faujasite", Angewandte. Chemie Int. Ed. 2009, 48, pp. 4813-4815.

Asci, Yavuz Selim et al. "Extraction of Glycolic Acid from Aqueous Solutions by Amberlite LA-2 in Difference Diluent Solvents" J. Chem Eng. Data 2009, 54, 2791-2794.

Bizek, Vladislav et al. "Amine Extraction of Hydroxycarboxylic Acids. 1. Extraction of Citric Acid with 1-Octanol/n-Heptane Solutions of Trialkylamine" Ind. Eng. Chem. Res. 1992, 31, 1554-1562.

Tamada, Janet A. et al. "Extraction of Carboxylic Acids with Amine Extractants. 1. Equilibria and Law of Mass Action Modeling" Ind. Eng. Chem. Res. 1990, 29, 1319-1326.

Smith, E. Lester, et al., "The Acid-Binding Properties of Long-Chain Aliphatic Amines", J.S.C.I., 67, Feb. 1948 pp. 48-51.

Walker, "Formaldehyde", ACS Monograph, Washington, DC., (1964), p. 95.

Eyal, A., et al. "Recovery and Concentration of Strong Mineral Acids from Dilute Solutions Through LLX III. A "Temperature Swing" Based Process", Solvent Extraction and Ion Exchange, 9 (2), pp. 223-236 (1991).

Eyal, A.M., et al. "Recovery and Concentration of Strong Mineral Acids from Dilute Soltions Through LLX. I: Review of Parameters for Adjusting Extractant Properties and Analysis of Process Options", Solvent Extraction and Ion Exchange, 9 (2), pp. 195-210 (1991).

Eyal, A.M., et al. "Recovery and Concentration of Strong Mineral Acids from Dilute Solutions Through LLX. II. Reversible Extraction with Branched-Chain Amines", Solvent Extraction and Ion Exchange, 9(2), pp. 211-222 (1991).

Eyal, Aharon, et al. "Extraction of Strong Mineral Acids by Organic Acid-Base Couples", Ind. Eng. Chem. Process Des. Dev., (1982), vol. 21, No. 2, pp. 334-337.

Handbook of Solvent Extraction, Krieger Publishing Company, Malabar, FL, 1991, pp. 275-501.

Treybal, Robert E. "Methods of Calculation II. Stagewise Contact, Multicomponent Systems", Liquid Extraction, $2^{nd}$ Edition, McGraw-Hill Book Company, New York. 1963, pp. 275-276.

Treybal, Robert E., Liquid Extraction, $2^{nd}$ Ed., McGraw-Hill Book Company, New York, NY, 1963, pp. 349-366.

Gerberich, H. Robert, et al., "Formaldehyde", Kirk-Othmer Encyclopedia of Chemical Technology, vol. 11, $4^{th}$ Edition, 1994, pp. 929-951.

Treybal, Robert E., Liquid Extraction, $2^{nd}$ Ed., McGraw Hill Book Company, 1963, pp. 248-252.

Lynch, Kathleen M., et al., "Improved Preparations of 3-Chloro-2(chloromethyl)-1-propene and 1,1-Dibromo-2,2-bis(chloromethyl)-cyclopropane: Intermediates in the Synthesis of [1.1.1]Propellane", J. Org. Chem, 60, (1995), pp. 4666-4668.

"Tray Design and Operation", Distillation Design, McGraw-Hill, New York (1992), Chapter 6, pp. 259-363.

"Packing Design and Operation", Distillation Design, McGraw-Hill, New York, (1992), Chapter 8, pp. 421-521.

Seader, J.D., Ph.D, et al., "Distillation", Perry's Handbook of Chemical Engineering, Section 13, $7^{th}$ Ed., McGraw-Hill Book Co. 1999.

Lee, Sang Young, et al., "Carbonylation of Formaldehyde over Ion Exchange Resin Catalysts. 1. Batch Reactor Studies", Ind. Eng. Chem. Res., 32, (1993), pp. 253-259.

Xu, Qiang, et al., "Preparation and Catalytic Application of Cationic Metal Carbonyls", Science and Technology in Catalysis, (2002), pp. 215-218.

Xu, Qiang, "Metal carbonyl cations: generation, characterization and catalytic application", Coordination Chemistry Reviews, 231, (2002), pp. 83-108.

Suzuki, S., et al., "Ethylene Glycol from Methanol and Synthesis Gas via Glycolic Acid", Catalytic Conversions of Synthesis Gas and Alcohols to Chemicals, (1984). pp. 221-247.

Wang, Zheng Bao, et al., Carbonylation of Formaldehyde with Carbon Monoxide over Cation-Exchange Resin Catalysts, Bull. Chem. Soc. Jpn., 72, (1999), pp. 1935-1940.

Sano, Tsunejo, et al., "Synthesis of 1,3-dioxolan-4-one from trioxane and carbon monoxide on HZSM-5 zeolite", Chem. Community, (1997), pp. 1827-1828.

Souma, Yoshie, "Carbonylation at Ambient Pressure in Strong Acids", Journal of Synthetic Organic Chemistry, vol. 41, No. 6, (1983), pp. 561-569.

Soma, Yoshie, et al., "Normal-Pressure CO Addition Reaction of Formaldehyde and Related Compounds on Copper Carbonyl Catalyst", Catalyst 23, (1981), pp. 48-50.

Li, Tao, et al., "Carbonylation of formaldehyde catalyzed by p-toluenesulfonic acid", Catalysis Today, 111, (2006), pp. 288-291.

Souma, Yoshie, et al., "Synthesis of tert.-Alkanoic acid catalyzed by $Cu(CO)^+_n$ and $Ag(CO)^+_2$ under atmospheric pressure", Catalysis Today, 36, (1997), pp. 91-97.

Hendriksen, Dan E., "Intermediates to Ethylene Glycol: Carbonylation of Formaldehyde Catalyzed by NAFION Solid Perfluorosulfonic Acid Resin", Prep. A.C.S. Div. Fuel Chem., 28, (1983), pp. 176-190.

(56) References Cited

OTHER PUBLICATIONS

Bhattacharyya, S.K., et al., "High-Pressure Synthesis of Glycolic Acid from Formaldehyde, Carbon Monoxide, and Water in Presence of Nickel, Cobalt, and Iron Catalysts", Advanced Catalysts, 9, (1957), pp. 625-635.

Wegescheider, Rud., et al., "Addition of Acid Anhydrides to Aldehydes and Ketones", Royal and Imperial University of Vienna, presented at the meeting of Nov. 4, 1909, pp. 1-47.

King, Walter D., et al., "The Acid-Catalyzed Reaction of Acetic Anhydride with Some Oxocanes", Journal of Applied Polymer Science, vol. 18, (1974) pp. 547-554.

He, Dehua, et al., "Condensation of formaldehyde and methyl formate to methyl glycolate and methyl methoxy acetate using heteropolyacids and their salts", Catalysis Today, 51, (1999), pp. 127-134.

Co-pending U.S. Appl. No. 12/889,045, filed Sep. 23, 2010, Scott Donald Barnicki, et al.

Co-pending U.S. Appl. No. 12/889,065, filed Sep. 23, 2010, Scott Donald Barnicki, et al.

Co-pending U.S. Appl. No. 13/208,399, filed Aug. 12, 2011, Scott Donald Barnicki, et al.

Co-pending U.S. Appl. No. 13/431,335, filed Mar. 27, 2012, Scott Donald Barnicki, et al.

Co-pending U.S. Appl. No. 13/431,308, filed Mar. 27, 2012, Scott Donald Barnicki, et al.

Co-pending U.S. Appl. No. 13/431,358, filed Mar. 27, 2012, Scott Donald Barnicki, et al.

Co-pending U.S. Appl. No. 13/431,369, filed Mar. 27, 2012, Scott Donald Barnicki, et al.

Co-pending U.S. Appl. No. 13/431,402, filed Mar. 27, 2012, Scott Donald Barnicki, et al.

Co-pending U.S. Appl. No. 13/431,386, filed Mar. 27, 2012, Scott Donald Barnicki, et al.

Co-pending U.S. Appl. No. 13/473,126, filed May 16, 2012, Daniel Latham Terrill, et al.

USPTO Notice of Allowance for U.S. Appl. No. 12/889,045 dated Jul. 18, 2012.

Notification of Transmittal of the International Search Report and the Written Opinion of the International Search Authority with Mail Date of Jun. 25, 2013 for International Application No. PCT/US2013/033501.

Notification of Transmittal of the International Search Report and the Written Opinion of the International Search Authority with Mail Date of Aug. 16, 2013 for International Application No. PCT/US2013/033410.

Notification of Transmittal of the International Search Report and the Written Opinion of the International Search Authority with Mail Date of Jun. 21, 2013 for International Application No. PCT/US2013/033520.

Notification of Transmittal of the International Search Report and the Written Opinion of the International Search Authority with Mail Date of Jun. 21, 2013 for International Application No. PCT/US2013/033411.

Cox et al. "Mechanistic Studies in Strong Acids . . . ", Journal of Organic Chemistry, vol. 51, No. 19 (Sep. 1, 1986), pp. 3619-3624.

USPTO Office Action dated Jul. 18, 2013 for U.S. Appl. No. 13/431,386.

USPTO Notice of Allowance for U.S. Appl. No. 13/431,358 dated Aug. 2, 2013.

USPTO Notice of Allowance for U.S. Appl. No. 13/431,386 dated Dec. 3, 2013.

USPTO Office Action for U.S. Appl. No. 13/431,369 dated Jan. 13, 2014.

USPTO Notice of Allowance for U.S. Appl. No. 13/431,402 dated Sep. 16, 2014.

Hou-Yong, Sun, et al. "Reactive extraction of glycolic acid in high content solution with tri-n-octylamine" Journal of Chemical Engineering of Chinese Universities, Feb. 2007, vol. 21 pp. 26-30.

Baniel, A., et al., "Acid-Base Couple Solvents in Recovery of Mineral Acids From Waste Streams", Proceedings of $2^{nd}$ International Conference on Separations Science and Technology, Oct. 1-4, 1989, pp. 667-674.

\* cited by examiner

HYDROCARBOXYLATION OF AQUEOUS FORMALDEHYDE USING A DEHYDRATING RECYCLE STREAM TO DECREASE WATER CONCENTRATION

FIELD OF THE INVENTION

This invention relates to a process for the production of glycolic acid or glycolic acid derivatives by the carbonylation of a readily available, economical, aqueous formaldehyde raw material. This invention discloses dehydration of the aqueous formaldehyde raw material using a dehydration stream comprising glycolic acid oligomers and/or methyl glycolate oligomers.

BACKGROUND OF THE INVENTION

Glycolic acid (also known as 2-hydroxyacetic acid or α-hydroxyacetic acid) can be used for many purposes including as a raw material to make ethylene glycol. Glycolic acid is prepared by the acid catalyzed reaction of carbon monoxide and formaldehyde in the presence of water, alcohols, and/or carboxylic acids. These processes often require high temperatures and pressures to proceed at practical rates. For example, glycolic acid typically is prepared by reacting formaldehyde with carbon monoxide and water in the presence of an acidic catalyst such as sulfuric acid under high temperature and pressure such as, for example, above 480 bar absolute (abbreviated herein as "bara"), and between 200 and 225° C. Alternatively, lower pressures may be employed in the presence of hydrogen fluoride as a catalyst and solvent. These processes, however, require expensive materials of construction and/or recovery and recycling schemes for hydrogen fluoride. Although water is required in the hydrocarboxylation reaction, excess water can decrease the reaction rate. Readily available and less expensive aqueous formaldehyde starting material typically contains excess water. Thus, there is a need for a robust and economical process for making glycolic acid from an aqueous formaldehyde starting material that can be accomplished at moderate temperatures and pressures and readily integrated into the overall process.

SUMMARY OF THE INVENTION

We have discovered that glycolic acid oligomers can be used to dehydrate an aqueous formaldehyde feed of a hydrocarboxylation reaction. The present invention provides in a first embodiment a process for the preparation of glycolic acid, comprising
(A) feeding carbon monoxide, aqueous formaldehyde, and a recycle dehydration stream to a hydrocarboxylation reaction zone to produce an effluent comprising glycolic acid, glycolic acid oligomers, and water;
(B) dehydrating the effluent to produce a first dehydration stream having a higher degree of polymerization (Dp) than the effluent and a water stream; and
(C) splitting the first dehydration stream into the recycle dehydration stream of step (A) and an intermediate stream.

The present invention provides in a second embodiment a process for the preparation of glycolic acid, comprising
(A) feeding carbon monoxide, aqueous formaldehyde, and a recycle dehydration stream to a hydrocarboxylation reaction zone to produce an effluent comprising glycolic acid, glycolic acid oligomers, methyl glycolate, methyl glycolate oligomers, and water;
(B) dehydrating the effluent in the presence of methanol to produce a first dehydration stream having a degree of polymerization (Dp) higher than the effluent and an overhead stream comprising water and methanol; and
(C) splitting the first dehydration stream into the recycle dehydration stream of step (A) and an intermediate stream.

DETAILED DESCRIPTION

The present invention provides in a first embodiment a process for the preparation of glycolic acid, comprising
(A) feeding carbon monoxide, aqueous formaldehyde, and a recycle dehydration stream to a hydrocarboxylation reaction zone to produce an effluent comprising glycolic acid, glycolic acid oligomers, and water;
(B) dehydrating the effluent to produce a first dehydration stream having a higher degree of polymerization (Dp) than the effluent and a water stream; and
(C) splitting the first dehydration stream into the recycle dehydration stream of step (A) and an intermediate stream.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

It is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

As used herein the term "and/or", when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "glycolic acid", as used herein, refers to the chemical compound, glycolic acid, also known as 2-hydroxyacetic acid. The term "glycolic acid oligomers", as used herein, refers to the reaction products of glycolic acid with itself, particularly the linear or cyclic esters formed by a reaction between the carboxyl group of one molecule and the alcohol group of another molecule. The "glycolic acid oligomers" include, but are not limited to, (2-hydroxyacetoxy)acetic acid (G2), 2-(2'-hydroxyacetoxy)acetoxyacetic acid (G3), and 2-(2'-(2''-hydroxyacetoxy)acetoxy)acetoxyacetic acid (G4).

The term "glycolic acid moiety", as used herein, refers to the $O-CH_2-CO_2$ segment of a molecule, for example, the segment in glycolic acid, a glycolic acid oligomer, methyl glycolate, a methyl glycolate oligomer, or an EG glycolate ester oligomer.

The term "methyl glycolate", as used herein, refers to the chemical compound methyl glycolate, also known as glycolic acid methyl ester. The term "methyl glycolate oligomers", as used herein refers to the reaction products of glycolic acid with methanol, particularly the compounds $H(O-CH_2-CO_2)_nCH_3$, wherein n is the number of glycolic acid moieties in each methyl glycolate oligomer: typically n is a number from 1 to 4.

The term, "degree of polymerization" or "Dp", as used herein, has its usual meaning of the number of monomeric repeat units in an oligomer. Specifically, the Dp is the average number of glycolic acid moieties in glycolic acid oligomers and/or the average number of glycolic acid moieties in methyl glycolate oligomers. When both glycolic acid oligomers and methyl glycolate oligomers are present the Dp of the glycolic acid oligomers and methyl glycolate oligomers can be calculated as the number of glycolic acid moieties divided by the summation of the number of moles of glycolic acid, methyl glycolate, glycolic acid oligomers, and methyl glycolate oligomers. Alternatively, NMR can give an average Dp for the mixture of glycolic acid oligomers and methyl glycolate oligomers.

The term "ester bond equivalents", as used herein refers to the number of bonds available to react with water and produce glycolic acid (i.e., one mole of ester bond equivalent reacts with water to produce a glycolic acid, lower order glycolic acid oligomer, methanol, and/or lower order methyl glycolate oligomer). For example each mole of G2 has one ester bond equivalent, each mole of G3 has 2, and each mole to G4 has 3. The ester bond equivalents for glycolic acid oligomers is one less than the Dp because glycolic acid, G1, does not have an ester bond. The methyl glycolate oligomers have ester bond equivalents equal to their degree of polymerization because methyl glycolate (with the methyl group attached to the glycolic acid moiety) has one ester bond.

The term "hydrocarboxylation reaction zone", as used herein, refers to the part of the process wherein the carbon monoxide, aqueous formaldehyde, and recycle dehydration stream are fed, and glycolic acid, glycolic acid oligomers, methyl glycolate, and/or methyl glycolate oligomers are produced. The term "effluent", as used herein, refers to the liquid stream exiting the hydrocarboxylation reaction zone comprising glycolic acid, glycolic acid oligomers, methyl glycolate, and/or methyl glycolate oligomers.

The term "homogeneous acid catalyst", as used herein, refers to an acid catalyst that is soluble or partly soluble in the reaction mixture under reaction conditions. The term "heterogeneous acid catalyst", as used herein, refers to solid acids including strong acid cation exchange resins, solidified acids, clay minerals, zeolites, inorganic oxides and composite oxides. Heterogeneous acid catalysts are characterized in having their acid function available on a solid surface without releasing acidity into the liquid reaction medium. The acid catalyst may be a Brønsted or Lewis acid as further described below.

The term "dehydrating", as used herein, refers to the removal of water, or a water equivalent such as methanol. The term "dehydration stream", as used herein, refers to the product of dehydrating the effluent from the hydrocarboxylation reaction zone.

The term "molar ratio", as used herein, refers to the moles of one component divided by the moles of another component. For example, if the molar ratio of carbon monoxide to formaldehyde is 10:1, then for every mole of formaldehyde, there are ten moles of carbon monoxide. Note that the water in any aqueous formaldehyde feed is not considered in the molar ratio of carbon monoxide to formaldehyde.

The terms "reactions of ethylene glycol and glycolic acid" and "reacting ethylene glycol and glycolic acid", as used herein, refer to the many reactions that occur when ethylene glycol and glycolic acid are present at typical reaction conditions. The reactions include reactions between ethylene glycol and glycolic acid and reactions of glycolic acid with itself. Additionally, the reactions include reactions between ethylene glycol, glycolic acid, and glycolic acid oligomers or other reaction products such as 2-hydroxyethyl 2-hydroxyacetate. The term "EG glycolate ester oligomers", as used herein, refers to the many reaction products of glycolate esters formed by "reacting ethylene glycol and glycolic acid". Examples include, but are not limited to 2-hydroxyethyl 2-hydroxyacetate, 1,2-ethanediyl bis(2-hydroxyacetate), 2'-[2''-(2'''-hydroxyacetoxy)acetoxy]ethyl 2-hydroxyacetate, 2'-(2''-[2'''-(2''''-hydroxyacetoxy)acetoxy]acetoxy)ethyl 2-hydroxyacetate, 2''-hydroxyethyl (2'-hydroxyacetoxy)acetate, 2'''-hydroxyethyl 2'-(2''-hydroxyacetoxy)acetoxyacetate, and 2''''-hydroxyethyl 2'-[2''-(2'''-hydroxyacetoxy)acetoxy]acetoxyacetate. EG glycolate ester oligomers can further comprise the glycolate esters formed by reacting ethylene glycol with methyl glycolate and methyl glycolate oligomers.

The term "splitting", as used herein, refers to the mechanical separation of material into two or more portions. For example, when a liquid stream is pumped down a pipe with a tee and a portion of the original stream is recycled to an upstream piece of equipment and a different portion of the original stream is further processed.

The first embodiment comprises (A) feeding carbon monoxide, aqueous formaldehyde, and a recycle dehydration stream to a hydrocarboxylation reaction zone to produce an effluent comprising glycolic acid, glycolic acid oligomers, and water.

The aqueous formaldehyde used in the hydrocarboxylation reaction typically comprises 35 to 85 weight percent formaldehyde. Other examples of formaldehyde levels in the aqueous formaldehyde feed are 40 to 70 weight percent and 40 to 60 weight percent. These ranges are typical concentrations that can be achieved with conventional formaldehyde processes without further distillation. Conventional formaldehyde processes are described in "Formaldehyde", Kirk-Othmer Encyclopedia, Vol. 11, 4$^{th}$ Edition, 1994. For example, commercially available formaldehyde typically contains approximately 55 weight percent formaldehyde in water. Other forms of formaldehyde may be present in the aqueous formaldehyde feedstock including trioxane or paraformaldehyde and linear oligomers and polymers of formaldehyde, i.e., poly(oxymethylene) glycols and derivatives thereof, formed from the polymerization or oligomerization of formaldehyde in water or other solvents. The term "formaldehyde", as used herein, is intended to include all the various forms of formaldehyde described above.

The recycle dehydration stream fed to the hydrocarboxylation reaction zone comprises glycolic acid and glycolic acid oligomers. It is a portion of the stream produced when the effluent from the hydrocarboxylation reaction is dehydrated as described in more detail below.

The carbon monoxide typically is supplied to the reaction mixture in sufficient excess to insure an adequate supply thereof for absorption by the formaldehyde and to retard side reactions such as, for example, the decomposition of the formaldehyde to carbon monoxide and hydrogen or other products. The amount of carbon monoxide useful for the carbonylation reaction ranges from a molar ratio of 1:1 to 1,000:1 or 1:1 to 100:1 or 1:1 to 20:1 or 1:1 to 10:1 or 2:1 to 20:1 or 2:1 to 10:1 of carbon monoxide to formaldehyde or formaldehyde equivalents.

The composition of the carbon monoxide stream required for hydrocarboxylation may comprise carbon monoxide, hydrogen, and carbon dioxide. For example, the carbon monoxide may be supplied in substantially pure form or as a mixture with other gases such as, for example, hydrogen, carbon dioxide, methane, nitrogen, noble gases (e.g., helium and argon), and the like. For example, the carbon monoxide need not be of high purity and may contain from 1% by volume to 99% by volume carbon monoxide. The remainder of the gas mixture may include such gases as, for example, nitrogen, hydrogen, water, carbon dioxide, noble gases, and paraffinic hydrocarbons having from one to four carbon atoms. In order to reduce compression costs, it is desirable for the carbon monoxide stream to comprise at least 95 mole % carbon monoxide, more preferably at least 99 mole %.

The carbon monoxide may be obtained from typical sources that are well known in the art. For example, the carbon monoxide may be provided by any of a number of methods known in the art including steam or carbon dioxide reforming of carbonaceous materials such as natural gas or petroleum derivatives; partial oxidation or gasification of carbonaceous materials, such as petroleum residuum, bituminous, sub bituminous, and anthracitic coals and cokes; lignite; oil shale; oil sands; peat; biomass; petroleum refining residues of cokes; and the like. For example, the carbon monoxide may be provided to the reaction mixture as a component of synthesis gas or "syngas", comprising carbon dioxide, carbon monoxide, and hydrogen.

The hydrocarboxylation process can be conducted under continuous, semi-continuous, and batch modes of operation and may utilize a variety of reactor types. Examples of suitable reactor types include, but are not limited to, stirred tank, continuous stirred tank, trickle bed, tower, slurry, and tubular reactors. A typical temperature range for the hydrocarboxylation reaction is from 80° C. to 220° C., 100° C. to 220° C., or 110° C. to 220° C. Other examples of the temperature range are from 110° C. to 210° C., 110° C. to 200° C., 110° C. to 190° C., 120° C. to 220° C., 120° C. to 210° C., 120° C. to 200° C., 140° C. to 220° C., 140° C. to 210° C., 150° C. to 210° C., or 160° C. to 210° C. Examples of pressure ranges for the hydrocarboxylation reaction are 35 bar gauge to 250 bar gauge, 35 bar gauge to 200 bar gauge, and 60 bar gauge to 200 bar gauge. In one example of the process, the aqueous formaldehyde comprises 35 weight percent to 85 weight percent formaldehyde, based on the total weight of the aqueous formaldehyde, the molar ratio of carbon monoxide to formaldehyde ranges from 1:1 to 10:1, and the hydrocarboxylation reaction zone is operated at a pressure of from 35 bar gauge to 200 bar gauge and a temperature of from 80° C. to 220° C. In another example of the process, the aqueous formaldehyde comprises 35 weight percent to 85 weight percent formaldehyde, based on the total weight of the aqueous formaldehyde, the molar ratio of carbon monoxide to formaldehyde ranges from 1:1 to 10:1, and the hydrocarboxylation reaction zone is operated at a pressure of from 35 bar gauge to 200 bar gauge and a temperature of from 160° C. to 210° C.

The presence of at least one acid catalyst, although not required for the reaction to proceed, greatly increases the rate of the carbonylation reaction and at the expense of side reactions. The acid catalyst may be of the Lewis or Brønsted types that are well understood by persons skilled in the art. The acid catalyst may be a heterogeneous acid catalyst or a homogeneous acid catalyst. Heterogeneous acid catalysts include sulfonic acid resins, silica-aluminate, silica-alumino-phosphates, heteropolyacids, supported heteropolyacids, sulfuric acid treated metal oxides, and phosphoric acid treated metal oxides. Homogeneous acid catalysts that are active in promoting the carbonylation process generally have pKa values in aqueous solution of less than 7. Representative examples of homogeneous acid catalysts are sulfonic acids, mineral acids, carboxylic acids, inorganic acid salts, and combinations thereof.

The hydrocarboxylation reactants may be introduced separately or in any sequence or combination to the hydrocarboxylation reaction zone. In addition, one or more reactants may be introduced at different locations in the reactor. For example, in a continuously operated process containing a catalyst bed in a reactor, the addition of aqueous formaldehyde may be staged throughout the reactor. In one aspect of our invention, the recycle dehydration stream and the aqueous formaldehyde steam are fed separately to the hydrocarboxylation zone. The reaction of the glycolic acid oligomers with water in the aqueous formaldehyde takes place in the hydrocarboxylation zone. In another aspect of our invention, the aqueous formaldehyde and recycle dehydration stream are contacted and allowed to react prior to the step (A) feeding into the hydrocarboxylation zone. How the aqueous formaldehyde and dehydration stream are contacted is not particularly limited. For example, the two liquid streams can be mixed in a tank with or without the addition of heat. In order to reduce by-product formation, it is desirable to set the residence time in the hydrocarboxylation reaction zone to give an outlet formaldehyde concentration of 5 weight percent or less. In addition to glycolic acid, the hydrocarboxylation process typically produces glycolic acid oligomers, water, and unreacted formaldehyde.

The process includes the step (B) of dehydrating the effluent to produce a first dehydration stream having a higher degree of polymerization (Dp) than the effluent and a water stream. The effluent from the hydrocarboxylation zone can be dehydrated by any means known to those skilled in the art. For example, the effluent can be heated in a temperature range of from 90° C. to 200° C. and at a pressure of 0.1 bar absolute to 1.5 bar absolute to cause oligomer formation and drive off water. The dehydrating can take place in many types of equipment including, for example, stirred tank, continuous stirred tank, trickle bed, tower, slurry, and tubular reactors. The dehydrating can take place in one or more stages in series or parallel.

The dehydrating is carried out to produce a first dehydration stream having a higher degree of polymerization than the hydrocarboxylation effluent and a water stream. As water is removed, the average chain length of the glycolic acid oligomers increases. The more water that is removed from the effluent during dehydrating, the longer the oligomer chains and the greater the degree of polymerization, Dp. Examples of degree of polymerization, Dp, include ranges of from 1.1 to 4.0, 1.1 to 3.5, 1.1 to 3.0, 1.1 to 2.8, 1.5 to 4.0, 1.5 to 3.5, 1.5 to 3.0, or 1.5 to 2.8. A first dehydration stream having a higher Dp than the effluent means that the Dp of the glycolic acid and glycolic acid oligomers in the first dehydration stream is larger than the Dp of the glycolic acid and glycolic acid oligomers in the effluent.

The first dehydration stream is split into a recycle dehydration stream which is fed to the hydrocarboxylation zone and an intermediate stream. The recycle dehydration stream reacts with the water in the aqueous formaldehyde to reduce the amount of water in the hydrocarboxylation zone while allowing the use of commercially available aqueous formaldehyde. Each ester bond equivalent reacts with water to produce a glycolic acid and/or lower order glycolic acid oligomer. The amount of water absorbed is a function of the number of ester bonds which is related to the degree of polymerization and the flow rate of the recycled dehydration stream. In one aspect of our invention, the feeding of the recycle dehydration stream and the aqueous formaldehyde of step (A) occurs at a molar ratio of ester bond equivalents to water (ester bond equivalents:water) of from 0.2:1 to 4:1 or 0.2:1 to 3:1 or 0.2:1 to 2.5:1 or 0.5:1 to 4:1 or 0.5:1 to 3:1 or 0.5:1 to 2.5:1 or 1:1 to 4:1 or 1:1 to 3:1 or 1:1 to 2.5:1.

The process also includes step (C), splitting the first dehydration stream into the recycle dehydration stream of step (A) and an intermediate stream. The splitting can take place by any means known to one skilled in the art. The recycle dehydration stream can be fed directly to the hydrocarboxylation reaction zone, contacted and reacted with the aqueous formaldehyde prior to being fed to the dehydrocarboxylation zone, and/or undergo additional processing steps between splitting from the first dehydration stream and feeding to the hydrocarboxylation reaction zone.

Our invention also includes processing the intermediate stream comprising glycolic acid and glycolic acid oligomers to produce ethylene glycol. Thus, one aspect of our invention further comprises (D) reacting the intermediate stream with a first ethylene glycol while simultaneously removing water to produce an esterification effluent comprising EG glycolate ester oligomers and glycolic acid oligomers and an overhead stream comprising water; and (E) reacting hydrogen with the esterification effluent to produce a second ethylene glycol, separating the second ethylene glycol into a product ethylene glycol and the first ethylene glycol, and recycling the first ethylene glycol to step (D).

The reacting of the intermediate stream comprising glycolic acid and glycolic acid oligomers with ethylene glycol while simultaneously removing water is readily recognized by one skilled in the art as an esterification reaction. The esterification can take place by any means known to those skilled in the art. For example, the intermediate stream can be heated to a temperature range of from 100° C. to 225° C. and at a pressure of 0.01 bar absolute to 1.0 bar absolute to cause EG glycolate ester oligomer and glycolic acid oligomer formation and drive off water. Any equipment that has sufficient hold up to allow the esterification reaction to proceed, allow a vapor phase to be produced, and allow for separation of the vapor phase from the liquid phase is suitable. The reacting of ethylene glycol with the intermediate stream may occur using at least one piece of equipment selected from the group consisting of an evaporator, a thin-film evaporator, a wiped-film evaporator, a flash vessel, a rectifying column, a stripping column, and a distillation column. Temperatures typically range from 100° C. to 225° C. or 150° C. to 200° C. and pressures typically range from 0.01 bar absolute to 1.1 bar absolute or 0.04 bar absolute to 0.25 bar absolute.

The EG glycolate ester oligomers may be hydrogenated as described below to produce ethylene glycol by contacting the EG glycolate ester oligomers with hydrogen in the presence of a suitable hydrogenation catalyst. The EG glycolate ester oligomers may be concentrated or purified by means known to one skilled in the art prior to hydrogenation. Alternatively, the EG glycolate ester oligomers can go directly from the reacting of step (D) to a hydrogenation reactor without additional processing steps. The ethylene glycol employed during the reacting of step (D) can be freshly added to the esterification reaction or obtained as a recycled portion of the crude ethylene glycol product. In another example, purified ethylene glycol may be recycled to the reacting of step (D). Considering the overall material balance, in theory 1 mole of ethylene glycol can be combined with 1 mole of glycolic acid ultimately to produce 2 moles of ethylene glycol, a fraction of which may be recycled to the reacting of step (D) and the remainder recovered as product.

The hydrogenation reaction can be conducted in the liquid or the gas phase using known processes. Typically, the EG glycolate ester oligomers are contacted with hydrogen under pressure in the presence of a catalyst effective for hydrogenation at temperatures from 150° C. to 300° C. Additional examples of temperatures ranges are from 200° C. to 250° C. Examples of typical pressure ranges are from 35 bara to 350 bara and 70 bara to 140 bara. Considerable latitude in the temperature and pressure of hydrogenation is possible depending upon the use and choice of hydrogenation catalyst and whether the process is conducted in the liquid or gas phase.

The hydrogenation catalyst may comprise any metal or combination of metals effective for the hydrogenation of esters to alcohols. Typical hydrogenation catalysts include, but are not limited to, at least one metal selected from Groups 8, 9, 10 of the Periodic Table of the Elements (1984 Revision by IUPAC), and copper. In addition, the hydrogenation catalyst may comprise at least one additional metal promoter selected from chromium, magnesium, barium, sodium, nickel, silver, lithium, potassium, cesium, zinc, cobalt, and gold. The term "metal", as used herein in the context of hydrogenation catalysts, is understood to include metals in their elemental form and compounds thereof such as, for example, metal oxides, salts, and complexes with organic ligands. For example, the hydrogenation catalyst can comprise a Raney nickel or a metal oxide. Typical metal oxide catalysts include, for example, copper chromite, copper oxide, or copper oxide in combination with the oxide of magnesium, barium, sodium, nickel, silver, lithium, potassium, cesium, zinc, cobalt, or mixtures thereof. In another example, the hydrogenation catalyst can comprise cobalt metal in combination with zinc and copper oxides.

The hydrogenation step of the process of the present invention may be conducted under continuous, semi-continuous, or batch modes of operation and may utilize a variety of reactor types. Examples of suitable reactor types include, but are not limited to, stirred tank, continuous stirred tank, trickle bed, tower, slurry, and tubular reactors. The catalyst should be dispersed throughout the reaction media to effectively assist contact of reactants and catalyst. The catalyst may be introduced as a liquid or as small particles which are conveniently slurried or suspended in the agitated reaction mixture. Typically, the catalyst is used in the form of a fixed bed or in slurry form through which reactants are continuously circulated in the liquid or gas phase.

The present invention provides in a second embodiment a process for the preparation of glycolic acid, comprising
  (A) feeding carbon monoxide, aqueous formaldehyde, and a recycle dehydration stream to a hydrocarboxylation reaction zone to produce an effluent comprising glycolic acid, glycolic acid oligomers, methyl glycolate, methyl glycolate oligomers, and water;
  (B) dehydrating the effluent in the presence of methanol to produce a first dehydration stream having a degree of polymerization (Dp) higher than the effluent and an overhead stream comprising water and methanol; and
  (C) splitting the first dehydration stream into the recycle dehydration stream of step (A) and an intermediate stream.

The various aspects of feeding carbon monoxide, aqueous formaldehyde, and a recycle dehydration stream to a hydrocarboxylation reaction zone, the aqueous formaldehyde, carbon monoxide and operation of the hydrocarboxylation reaction zone, and the splitting of the first dehydration stream into the recycle dehydration stream of step (A) and an intermediate stream of the first embodiment apply to this embodiment as well.

The process of the second embodiment comprises step (A) feeding carbon monoxide, aqueous formaldehyde, and a recycle dehydration stream to a hydrocarboxylation reaction zone to produce an effluent comprising glycolic acid, glycolic acid oligomers, methyl glycolate, methyl glycolate oligomers, and water. The recycle dehydration stream fed to the hydrocarboxylation reaction zone comprises glycolic acid, glycolic acid oligomers, methyl glycolate, and methyl glycolate oligomers. It is a portion of the stream produced when the effluent from the hydrocarboxylation reaction is dehydrated as described in more detail below.

The hydrocarboxylation reactants may be introduced separately or in any sequence or combination to the hydrocarboxylation reaction zone. In addition, one or more reactants may be introduced at different locations in the reactor. For example, in a continuously operated process containing a catalyst bed in a reactor, the addition of aqueous formaldehyde may be staged throughout the reactor. In one aspect of our invention, the recycle dehydration stream and the aqueous formaldehyde steam are fed separately to the hydrocarboxylation reaction zone. The reaction of the glycolic acid oligomers, methyl glycolate, and methyl glycolate oligomers with water in the aqueous formaldehyde takes place in the hydrocarboxylation reaction zone. In another aspect of our invention, the aqueous formaldehyde and recycle dehydration stream are contacted and allowed to react prior to the step (A) feeding into the hydrocarboxylation reaction zone. How the aqueous formaldehyde and dehydration stream are contacted is not particularly limited. For example, the two liquid streams can be mixed in a tank with or without the addition of heat. In order to reduce by-product formation, it is desirable to set the residence time in the hydrocarboxylation reaction zone to give an outlet formaldehyde concentration of 5 weight percent or less. In addition to glycolic acid, the hydrocarboxylation process typically produces glycolic acid oligomers, methyl glycolate, methyl glycolate oligomers, water, and unreacted formaldehyde.

The process includes the step (B) of dehydrating the effluent in the presence of methanol to produce a first dehydration stream having a degree of polymerization (Dp) higher than the effluent and an overhead stream comprising methanol and water. Methanol is typically added as a reactant in the dehydrating step with excess methanol (i.e., unreacted or the byproduct of methyl glycolate oligomerization) removed in the overhead stream. The effluent from the hydrocarboxylation zone can be dehydrated by any means known to those skilled in the art. For example, the effluent can be heated in a temperature range of from 60° C. to 250° C. and at a pressure of 0.5 bar absolute to 1.5 bar absolute to cause oligomer formation and drive off water and methanol. The dehydrating can take place in many types of equipment including, for example, stirred tank, continuous stirred tank, trickle bed, tower, slurry, and tubular reactors. The dehydrating can take place in one or more stages in series or parallel.

The dehydrating of the effluent is carried out in the presence of methanol to produce a first dehydration stream having a higher degree of polymerization than the hydrocarboxylation effluent and an overhead stream comprising water and methanol. As water and methanol are removed, the average chain length of the glycolic acid oligomers and methyl glycolate oligomers increases. The more water and methanol that are removed from the effluent during dehydrating, the longer the oligomer chains and the greater the degree of polymerization, Dp. Examples of degree of polymerization, Dp, include ranges of from 1.1 to 4.0, 1.1 to 3.5, 1.1 to 3.0, 1.1 to 2.8, 1.5 to 4.0, 1.5 to 3.5, 1.5 to 3.0, or 1.5 to 2.8. A first dehydration stream having a higher Dp than the effluent means that the Dp of the glycolic acid, glycolic acid oligomers, methyl glycolate, and methyl glycolate oligomers in the first dehydration stream is larger than the Dp of the glycolic acid, glycolic acid oligomers, methyl glycolate, and methyl glycolate oligomers in the effluent.

The first dehydration stream is split into a recycle dehydration stream which is fed to the hydrocarboxylation zone and an intermediate stream. The recycle dehydration stream reacts with the water in the aqueous formaldehyde to reduce the amount of water in the hydrocarboxylation zone while allowing the use of commercially available aqueous formaldehyde. Each ester bond equivalent reacts with water to produce a glycolic acid, lower order glycolic acid oligomer, methanol, and/or lower order methyl glycolate oligomer. The amount of water absorbed is a function of the number of ester bonds which is related to the degree of polymerization, the relative amount of glycolic acid oligomers and methyl glycolate oligomers, and the flow rate of the recycled dehydration stream. In one aspect of our invention, the feeding of the recycle dehydration stream and the aqueous formaldehyde of step (A) occurs at a molar ratio of ester bond equivalents to water (ester bond equivalents:water) of from 0.2:1 to 4:1 or 0.2:1 to 3:1 or 0.2:1 to 2.5:1 or 0.5:1 to 4:1 or 0.5:1 to 3:1 or 0.5:1 to 2.5:1 or 1:1 to 4:1 or 1:1 to 3:1 or 1:1 to 2.5:1.

The process also includes step (C), splitting the first dehydration stream into the recycle dehydration stream of step (A) and an intermediate stream. The splitting can take place by any means known to one skilled in the art. The recycle dehydration stream can be fed directly to the hydrocarboxylation zone, contacted and reacted with the aqueous formaldehyde prior to being fed to the dehydrocarboxylation zone, and/or undergo additional processing steps between splitting from the first dehydration stream and feeding to the hydrocarboxylation zone.

Our invention also includes processing the intermediate stream comprising glycolic acid, glycolic acid oligomers, methyl glycolate, and methyl glycolate oligomers to produce ethylene glycol. Thus, one aspect of our invention further comprises (D) reacting the intermediate stream with a first ethylene glycol while simultaneously removing water and methanol to produce an esterification effluent comprising EG glycolate ester oligomers and glycolic acid oligomers and an overhead stream comprising water and methanol; and (E) reacting hydrogen with the esterification effluent to produce a second ethylene glycol, separating the second ethylene glycol into a product ethylene glycol and the first ethylene glycol, and recycling the first ethylene glycol to step (D).

The reacting of the intermediate stream comprising glycolic acid, glycolic acid oligomers, methyl glycolate, and methyl glycolate oligomers with ethylene glycol while simultaneously removing water and methanol is readily recognized by one skilled in the art as an esterification reaction. The esterification can take place by any means known to those skilled in the art. For example, the intermediate stream can be heated in a temperature range of from 100° C. to 225° C. and at a pressure of 0.01 bar absolute to 1.0 bar absolute to cause EG glycolate ester oligomer, glycolic acid oligomer, and methyl glycolate oligomer formation and drive off water and methanol. Any equipment that has sufficient hold up to allow the esterification reaction to proceed, allow a vapor phase to be produced, and allow for separation of the vapor phase from the liquid phase is suitable. The reacting with ethylene glycol may occur in at least one piece of equipment selected from the group consisting of an evaporator, a thin-film evaporator, a wiped-film evaporator, a flash vessel, a rectifying column, a stripping column, and a distillation column. Temperatures typically range from 100° C. to 225° C. or 150° C. to 200° C. and pressures typically range from 0.01 bar absolute to 1.1 bar absolute or 0.04 bar absolute to 0.25 bar absolute.

The EG glycolate ester oligomers may be hydrogenated as described herein above to produce ethylene glycol by contacting the EG glycolate ester oligomers with hydrogen in the presence of a suitable hydrogenation catalyst. The EG glycolate ester oligomers may be concentrated or purified by means known to one skilled in the art prior to hydrogenation. Alternatively, the EG glycolate ester oligomers can go directly from the reacting of step (D) to a hydrogenation reactor without additional processing steps. The ethylene glycol employed during the reacting of step (D) can be freshly added to the esterification reaction or obtained as a recycled portion of the crude ethylene glycol product. In another example, purified ethylene glycol may be recycled to the reacting of step (D). Considering the overall material balance, in theory 1 mole of ethylene glycol can be combined with 1 mole of glycolic acid ultimately to produce 2 moles of ethylene glycol, a fraction of which may be recycled to the reacting of step (D) and the remainder recovered as product.

One skilled in the art recognizes that glycolic acid oligomers are often esterified, for example, with ethylene glycol, prior to hydrogenation to increase the reaction rate. Methyl glycolate oligomers will hydrogenate at a faster reaction rate than glycolic acid oligomers. Therefore, another aspect of the process of the present embodiment further comprises hydrogenating the intermediate stream comprising methyl glycolate oligomers to produce ethylene glycol. The hydrogenation reaction conditions discussed above are applicable to the direct hydrogenation of an intermediate stream comprising methyl glycolate oligomers.

EXAMPLES

The compounds and abbreviations given in Table 1 are used throughout the Examples section. Structures for each compound are also given.

TABLE 1

| Compound Names, Structures, and Abbreviation | | |
|---|---|---|
| Name | Structure | Code |
| Glycolic Acid | HO–CH2–C(=O)–OH | G1 |
| (2-hydroxyacetoxy)-acetic acid | HO–CH2–C(=O)–O–CH2–C(=O)–OH | G2 |
| 2-(2'-hydroxyacetoxy)-acetoxyacetic acid | HO–CH2–C(=O)–O–CH2–C(=O)–O–CH2–C(=O)–OH | G3 |
| 2-(2'-(2''-hydroxyacetoxy)-acetoxy)acetoxyacetic acid | HO–CH2–C(=O)–O–CH2–C(=O)–O–CH2–C(=O)–O–CH2–C(=O)–OH | G4 |
| Propionic Acid | CH3–CH2–C(=O)–OH | A3 |
| Formaldehyde | H–C(=O)–H | F0 |
| Methylene Glycol | HO–CH2–OH | F1 |

TABLE 1-continued

Compound Names, Structures, and Abbreviation

| Name | Structure | Code |
|---|---|---|
| Polymethylene glycol | HO-(-O-)$_n$-H, n = 2-10 | Fn, n = 2-10 |
| Formic Acid | H-C(=O)-OH | A1 |
| Diglycolic Acid | HO-C(=O)-CH$_2$-O-CH$_2$-C(=O)-OH | DG |
| 2-Methoxyacetic Acid | HO-C(=O)-CH$_2$-O-CH$_3$ | MGH |
| Methyl Formate | H-C(=O)-O-CH$_3$ | MF |
| Methyl Glycolate | HO-CH$_2$-C(=O)-O-CH$_3$ | MG |
| (2-hydroxyacetoxy)-acetic acid methyl ester | HO-CH$_2$-C(=O)-O-CH$_2$-C(=O)-O-CH$_3$ | MG2 |
| 2-(2'-hydroxyacetoxy)-acetoxyacetic acid methyl ester | HO-CH$_2$-C(=O)-O-CH$_2$-C(=O)-O-CH$_2$-C(=O)-O-CH$_3$ | MG3 |
| Methyl 2-methoxyacetate | CH$_3$-O-CH$_2$-C(=O)-O-CH$_3$ | MGM |

Materials—Sulfuric acid was purchased from J. T. Baker and trifluoromethanesulfonic acid (also known as triflic acid) was purchased from SynQuest Labs, Inc. Paraformaldehyde (90% min) was purchased from Kodak. All chemicals were used as received except as noted below.

Gas Chromatography (GC). The components of samples were first reacted with BSTFA in the presence of pyridine to the corresponding TMS-derivatives including water, which were then separated and quantified by an internal standard (decane or dodecane) wt % calibrated GC method. The volume ratio of sample to derivatization reagent (BSTFA) and pyridine (containing the internal standard compound) was 0.1 g: 1 ml:0.2 ml in a GC vial, which was heated at 80° C. for 30 minutes to ensure complete derivatization. The GC method uses a DB-1301 capillary column or equivalent (6% cyanopropylphenyl/94% dimethylpolysiloxane stationary phase, 60 meters×0.32 mm ID×1.0 um film thickness), a split injector (at 280° C.), a flame ionization detector (at 300° C.), helium carrier gas at a constant linear velocity of 27 cm/sec (a Shimadzu GC 2010 or equivalent) or at an initial column head pressure of 17 psig, an oven temperature program of 80° C. initial temp for 6 min, 4° C./min temp ramp to 150° C. held for 0 min and 10° C./min temp ramp to 290° C. for 17.5 min final hold time. 1 μl of the prepared sample solution was injected with a split ratio of 40:1. Analytes include, for example: MeOH, A1, water, G1 and higher oligomers, DG, and MG.

High Pressure Liquid Chromatography (HPLC). Samples were analyzed by liquid chromatography for glycolic acid using size-exclusion chromatography after samples were subjected to acid hydrolysis in aqueous 25% v/v $H_2SO_4$ at 80° C. for 30 minutes. The analytes were separated on a Hamilton PRP X300 column using a 10 mM $H_3PO_4$ mobile phase with a 1-20% v/v acetonitrile gradient. The eluting components were monitored using a UV detector set at 210 nm and their concentrations calculated based on calibration using external standards. Formaldehyde was determined by liquid chromatographic separation of the 2,4-dinitrophenylhydrazone derivative of formaldehyde and its subsequent detection by UV at 360 nm. The same acid hydrolysate from the procedure above was reacted with dinitrophenylhydrazine, then analyzed using a Phenomenex Luna C8 column using a 1:1 water:acetonitrile mobile phase under isocratic conditions. The formaldehyde concentration was calculated based on calibration using external standards.

X-ray method for triflic acid. Reactor effluent samples were analyzed for sulfur using a wavelength dispersive x-ray fluorescence (WDXRF) semi-quantitative application called UNIQUANT™ (UQ). UQ affords standardless XRF analysis of samples. The data were mathematically corrected for matrix differences between calibration standards and samples as well as absorption and enhancement effects; i.e., inter-element effects. Instrument conditions for sulfur analysis were: Line, $K_\alpha$; kV, 40; mA, 60; Filter, none; Collimator Spacing (mm), 150; Crystal, Ge III-C; Peak Angle (2q), 110.6712; Detector, flow; PHD Lower, 35; PHD Upper, 70; Collimator Mask (mm), 30; Peak time (s), 30. Sulfur weight fraction numbers were converted to triflic acid weight equivalents by the factor 4.68 (ratio of molecular weight of triflic acid to that of sulfur).

NMR Method for hydrocarboxylation product sample analysis. $DCl/D_2O$/propionic acid stock solution preparation: $D_2O$ (99.99%, CIL) (74.606 g), 35% DCl in D2O (CIL) (47.755 g) and propionic acid (JT Baker) (2.198 g) were thoroughly mixed in a bottle to give 0.01765 g of propionic acid per g of stock solution. Hydrocarboxylation product sample preparation for $^1H$ NMR analysis: About 50 mg of hydrocarboxylation sample was transferred to a 2 dram screw top vial with a phenolic cap with a polypropylene liner and the exact mass of the sample was recorded. Then 0.8288 g of stock solution was added and the mixture was heated in a heat block for 1 hour at 60° C. The vial was allowed to cool to room temperature and then the solution was transferred to an NMR tube. $^1H$ NMR analysis: $^1H$ NMR was recorded using 30 seconds pulse delay, 90 degree pulse angle, 16 scans and $D_2O$ lock solvent. The spectrum was referenced to the $CH_3$ triplet of propionic acid (1.15 ppm). The meq/g concentrations of the following components were obtained from peak integrations (A1 δ 8.36 ppm, F0 δ 4.99, 4.94 ppm, $MeOCH_2OH$ δ 4.83 ppm, MGH δ 3.52 ppm, MG δ 3.84 ppm, MGM δ 3.85 ppm, G1 δ 4.35 ppm, MeOH δ 3.47 ppm, MeOPr (methyl propionate) δ 3.76 ppm, HOPr (ISTD) δ 2.50 ppm).

Selectivity—

Examples 1-9 and 21-26 were analyzed by HPLC where during sample preparation the glycolic acid oligomers and glycolic acid moieties in methyl glycolate and methyl glycolate oligomers were converted to free glycolic acid and one mole of free methanol was produced for each mole of methyl glycolate and methyl glycolate oligomer. The selectivity of glycolic acid, for example, was calculated as the total moles of new glycolic acid from the HPLC method (note that new glycolic acid is the glycolic acid formed in the reaction, i.e., the glycolic acid in the product minus the glycolic acid in the feed) divided by moles formaldehyde reacted.

Selectivities to glycolic acid were calculated for Examples 13-20 based upon NMR results for formaldehyde at the start and after reaction and GC results for byproduct formation. The by-products measured were moles of methyl formate, moles of formic acid and moles of diglycolic acid. The selectivity was calculated as the total moles of formaldehyde consumed minus moles of by-products formed divided by the moles of formaldehyde consumed. One skilled in the art recognizes that the moles of diglycolic acid are multiplied by two in the selectivity calculation since it has two glycolic acid moieties.

Space time yield (STY) was calculated as the moles of glycolic acid produced per liter of reactor volume per hour.

The following examples illustrate the effect of feed water content, temperature, pressure, and catalyst level on the hydrocarboxylation of aqueous formaldehyde with sulfuric acid as catalyst.

Example 1

The continuous hydrocarboxylation was carried out using a reactor system containing a Zirconium autoclave (125 ml nominal volume) and associated feed and product storage equipment. The high pressure autoclave was fitted with a hollow shaft Rushton turbine impeller (for gas introduction and dispersion), baffles, thermowell, gas inlet tube, and sip tube to maintain liquid level at approximately 90 ml and to provide an exit for product effluent. The autoclave was heated electrically by a band heater, with temperature control provided by feedback via a K-type thermocouple in the autoclave thermowell.

Pure carbon monoxide gas (>99.9%) was fed to the autoclave via a high pressure flow controller. The gas entered the body of the autoclave via grooves in the impeller bearings. The off gas flow rate was monitored by a dry bubble-type flow meter. The flow rate of the liquid feed was controlled to a precision of 0.001 ml/min with double-barreled 500 ml high-precision syringe pumps connected to stirred feed vessels.

Reactor effluent passed through heated Hastelloy tubing, an automatic pressure control valve (research control valve), and into a 1.0 L heatable Hastelloy collection vessel. The effluent collection vessel was fitted with a chilled coiled condenser. The gas outlet from the effluent tank was connected to a manual back pressure regulator to maintain vessel pressure at 40-100 psig. Temperatures, pressures, and other relevant system parameters were recorded automatically by a distributed control system.

Feed 1 (0.68 g/min), having the composition given in Table 2 was fed to the reactor. The feed mixture was prepared by mixing water, $H_2SO_4$ and glycolic acid in a tank heated to 60° C. Paraformaldehyde was added with stirring until complete dissolution occurred. The feed was kept at 60° C. throughout the reaction period to ensure no solid formaldehyde precipitated. The feed molar ratios, pressure, temperature, and residence time are given in Table 3. Carbon monoxide was fed at a rate of 998 SCCM. The reaction was run at a pressure of 1502 psig and a temperature of 170° C. with a residence time of 180 minutes.

Samples of the hydrocarboxylation reaction were analyzed by HPLC. Conversion, space-time yield, and selectivity of reacted formaldehyde to end products are summarized in Table 4. Any glycolic acid moieties fed were subtracted out for conversion, selectivity, and space-time yield calculations.

Examples 2-6

Example 1 was repeated with the feed rate and composition shown in Table 2. The feed molar ratios, pressure, temperature, and residence time are given in Table 3. Conversion, space-time yield, and selectivity of reacted formaldehyde to end products are summarized in Table 4.

TABLE 2

| Feed 1: Rate and Composition in weight percent | | | | | |
|---|---|---|---|---|---|
| Ex | g/min | Paraformaldehyde | Water | G1 | $H_2SO_4$ |
| 1 | 0.68 | 13.8 | 8.3 | 70.2 | 7.7 |
| 2 | 1.01 | 13.8 | 11.7 | 70.0 | 4.5 |

TABLE 2-continued

Feed 1: Rate and Composition in weight percent

| Ex | g/min | Paraformaldehyde | Water | G1 | $H_2SO_4$ |
|----|-------|------------------|-------|------|-----------|
| 3  | 1.01  | 13.8             | 11.6  | 70.0 | 4.5       |
| 4  | 1.66  | 13.0             | 17.2  | 66.0 | 3.8       |
| 5  | 1.02  | 14.4             | 4.3   | 73.2 | 8.0       |
| 6  | 0.94  | 29.8             | 28.6  | 37.8 | 3.8       |

TABLE 3

Overall Feed Ratios and Reaction Conditions

| | Feed Molar Ratio | | | Temp | Press | Res Time |
|---|---|---|---|---|---|---|
| Ex | F0 | water | G1 | $H_2SO_4$ | Celsius | psig | minutes |
| 1 | 1.0 | 1.0 | 2.0 | 0.170 | 170 | 1502 | 180 |
| 2 | 1.0 | 1.4 | 2.0 | 0.100 | 200 | 699  | 120 |
| 3 | 1.0 | 1.4 | 2.0 | 0.100 | 190 | 703  | 120 |
| 4 | 1.0 | 2.2 | 2.0 | 0.089 | 205 | 2603 | 72  |
| 5 | 1.0 | 0.5 | 2.0 | 0.170 | 190 | 1901 | 120 |
| 6 | 1.0 | 1.6 | 0.5 | 0.039 | 205 | 2605 | 120 |

TABLE 4

Selectivity, Conversion, and Space-Time Yield Results

| | % F0 | Molar Selectivities | | | | | Space-Time Yield |
|---|---|---|---|---|---|---|---|
| Ex | Conv | G1 | A1 | DG | MGH | MeOH | gmol/l-hr |
| 1 | 92 | 94.06 | 1.06  | 3.82  | 0.00  | 1.06 | 1.73 |
| 2 | 87 | 64.56 | 10.72 | 5.56  | 16.86 | 2.29 | 1.05 |
| 3 | 85 | 70.00 | 10.80 | 3.00  | 10.40 | 5.70 | 1.55 |
| 4 | 93 | 89.22 | 2.90  | 4.12  | 1.72  | 2.04 | 3.55 |
| 5 | 97 | 84.63 | 1.24  | 11.97 | 1.85  | 0.32 | 2.51 |
| 6 | 95 | 89.96 | 3.04  | 2.91  | 2.11  | 1.98 | 4.94 |

The following examples illustrate the effect of feed water content on the rate of hydrocarboxylation of paraformaldehyde in glycolic acid with triflic acid as a catalyst. For the same catalyst loading, temperature, pressure and residence time, the space time yield of moles glycolic acid produced per reactor liter per hour decreased from 2.6 to 2.0 to 1.6 as the moles of water per mole of formaldehyde increased for 0.3:1 to 0.7:1 to 1.4:1, respectively. At a molar ratio of 1.4:1, the resulting aqueous formaldehyde is 54 weight percent formaldehyde in water which, although made by mixing paraformaldehyde and water, is the same concentration as commercially available aqueous formaldehyde.

Example 7

Example 1 was repeated using a Hastelloy 276C autoclave and with the feed rate, molar feed ratios, and operating conditions of temperature, pressure, and residence time given in Table 5. The feed mixture was prepared by mixing, water, triflic acid, and glycolic acid in a tank heated to 60° C. Paraformaldehyde was added with stirring until complete dissolution occurred. The feed was kept at 60° C. throughout the reaction period to ensure no solid formaldehyde precipitated.

Conversion, space-time yield, and selectivity of reacted formaldehyde to end products are summarized in Table 6. Calculations of conversion, space-time yield, and selectivity were based only on fresh formaldehyde feed and did not include glycolic acid already present in the feed mixture.

Process temperature, pressure, feed flow rate, and feed composition were maintained constant for 24 to 72 hours. Each point represents the average analysis at each set of conditions. During analysis by high pressure liquid chromatography, glycolic acid oligomers and other forms of glycolic acid were hydrolyzed and converted to free monomeric glycolic acid equivalents. The selectivity of formaldehyde to glycolic acid is reported based upon free glycolic acid equivalents. Methanol was present as both free methanol and methyl glycolate, and was converted to free methanol and glycolic acid by the analytical method.

Conversion is defined as the moles of formaldehyde (as paraformaldehyde) reacted divided by moles of formaldehyde fed. Molar selectivity is defined as the moles of each hydrocarboxylation reaction product species created per mole of formaldehyde reacted. Selectivity calculations do not include unreacted formaldehyde.

Examples 8 and 9

Example 7 was repeated with the molar ratio of water in each feed as given in Table 5. Conversion, space-time yield, and selectivity of reacted formaldehyde to end products are summarized in Table 6.

TABLE 5

Feed Rate, Feed Ratios, and Reaction Conditions

| | Feed Rate | Feed Molar Ratios | | | | Temp. | Pressure | Residence Time |
|---|---|---|---|---|---|---|---|---|
| Example | g/min | F0 | $H_2O$ | G1 | Triflic | Celsius | Bara | Minutes |
| 7 | 1.03 | 1.0 | 0.3 | 1.0 | 0.030 | 170 | 83.8 | 95 |
| 8 | 1.03 | 1.0 | 0.7 | 1.0 | 0.030 | 170 | 83.8 | 95 |
| 9 | 1.03 | 1.0 | 1.4 | 1.0 | 0.030 | 170 | 83.8 | 95 |

TABLE 6

Molar Selectivity, Conversion, and Space-Time Yield Results

| Ex | F0 Conv. | G1 | A1 | MeOH | MGH | DG | STY mol/liter/hr |
|---|---|---|---|---|---|---|---|
| 7 | 73.4% | 93.5% | 2.7%  | 0.9% | 2.2%  | 1.2% | 2.6 |
| 8 | 63.5% | 84.5% | 7.1%  | 2.0% | 5.9%  | 2.4% | 2.0 |
| 9 | 61.4% | 68.1% | 15.1% | 4.6% | 13.5% | 3.1% | 1.6 |

Example 10

Preparation of methyl glycolate oligomer. A 1-liter, 5-neck, round-bottom flask was fitted with a distillation head, thermocouple, mechanical stirrer, and heating mantle. To this flask was added 244.4 grams of methyl glycolate followed by 1.0 g of concentrated sulfuric acid. The mixture was heated to 160° C. while distilling methanol overhead. Heating was discontinued after collecting 47.5 g of distillate. The oligomer was analyzed by $^1$H NMR spectroscopy. $^1$H NMR spectroscopy is a common method for determining the degree of polymerization and one skilled in the art knows how to use the data to calculate Dp for the glycolic acid oligomer and methyl glycolate oligomer. Dp of the oligomer (n) was calculated by the following formula for the NMR Data: Dp of the oligomer (n)=(3/2)×(methylene integration/methyl integration)=(3/2)×(55.79/27.42)=3.05.

Example 11

To determine the rate of water scrubbing from aqueous formaldehyde by the oligomer in the presence of triflic acid, the following experiment was conducted: 33.0 g of methyl glycolate oligomer of Example 13, and 7.93 g of 50% Georgia Pacific (GP) formaldehyde, and 1.2 wt % of triflic acid were mixed and heated at 110° C. in a glass MULTIMAX reactor (Mettler Toledo, Columbus Ohio) equipped with a reflux condenser. A faint yellow viscous solution was observed shortly. Samples were taken at 5 min, 20 min, 30 min and 1 h. It was then cooled to room temperature. The levels of the water in the samples were analyzed by gas chromatography. The amount of water at each time increment is given in Table 7.

TABLE 7

Water concentration of scrubbing reaction

| Time (min.) | Water (wt %) |
|---|---|
| 0 | 9.7 |
| 5 | 3.8 |
| 20 | 3.6 |
| 30 | 3.4 |
| 60 | 3.4 |

Example 12

Multiple batches of methyl glycolate oligomer, with a Dp of, for example, 2.6 and 2.77, were prepared in a fashion representative of the following procedure. A 50-liter round bottom flask with a bottom valve was equipped with an electrical heating mantle, thermocouple and temperature controller, air-driven impeller, distillation column/reflux splitter/condenser, 2-liter addition flask and vacuum pump for preparing methyl glycolate oligomers. The distillation column comprised a vacuum jacketed glass column, 51 mm inside diameter by 51 cm tall, 51 cm of 6 mm corrugated metal packing pieces, a timed liquid-dividing reflux splitter, a 1-liter graduated receiver pot, water cooled condenser, nitrogen sweep, and vacuum connection line. To the reaction flask was charged 24,425 grams of 70 weight percent glycolic acid in water and 112.5 grams of trifluoromethanesulfonic acid in 900 grams of water. The flask was heated to about 100° C. with agitation, and the vacuum was set to about 0.13 bara, with the timed liquid-dividing reflux splitter set to 100% takeoff. The flask temperature was gradually increased up to about 110° C. and water removal continued until about 9850 grams had been removed via the receiver. At this point system pressure was raised to atmospheric, and 22,500 grams of methanol was charged to the flask via the addition flask, with stirring. The methanol addition cooled the vessel and the heat input was increased to bring the system back up to reflux temperature and held for one hour. Methanol and water were then distilled off until the pot temperature reached 110° C. An additional 22,500 grams of methanol was added and the distillation was repeated until the pot temperature reached 110° C. The methanol addition and distillation was repeated a third time. After the fourth methanol addition, the distillation was continued until the pot temperature reached 85° C. The system pressure was reset to 0.18 bara, and distillation was continued at a 3-1 reflux ratio until the base temperature reached 120° C. At this end point the contents were sampled and weighed, analyzed by gas chromatography, and found to comprise 13,335 grams of methyl glycolate oligomers, with an average Dp of 2.6 and less than 0.1 wt % water and methanol.

The following examples illustrate the effects of methyl glycolate oligomer scrubbing of aqueous formaldehyde, the amount of triflic acid, and temperature on batch hydrocarboxylation reaction formaldehyde conversion.

Example 13

Methyl glycolate oligomer made using the general procedure of Example 12 with an average Dp of 2.77 (35.94 g, 0.19 mol), 50% GP formaldehyde (8.11 g, 0.14 mol), triflic acid (0.27 g, 1.77 mmol) and dimethyl sulfone internal standard (0.47 g, 5.0 mmol) were mixed and heated in a glass MULTIMAX with reflux condenser at 110° C. for 30 min. A faint yellow viscous solution was obtained. The amount of water at the start of the scrubbing was calculated based upon the amount of formaldehyde charged and the amount of water in the MULTIMAX after the 30 minutes of scrubbing at reflux was determined by gas chromatography. The molar percent of water absorbed (moles water charged−moles water final)/moles water charged was calculated and is reported in Table 8. Then the viscous liquid was transferred to a 50 mL Hastelloy 276C autoclave. The autoclave was, assembled and pressurized with 200 psi of nitrogen and vented. This purging procedure was repeated two times. To remove nitrogen from the autoclave, it was purged with 200 psig of CO. Then the reactor was pressurized with 200 psig of CO and heated with stirring to 120° C. Once the desired temperature was reached, the reactor was pressurized to 1000 psig CO and the pressure was maintained from the surge tank. After 1 hour hold time, the reactor was cooled to room temperature and vented. Finally the autoclave was purged with nitrogen and unloaded. The reaction content was analyzed using NMR (for formaldehyde and methyl glycolate oligomers) and Gas Chromatography (for water, formic acid, diglycolic acid and methyl formate). Triflic acid reported is the sum of triflic acid charged to the MULTIMAX and triflic acid in the methyl glycolate oligomer. Table 8 gives formaldehyde conversion along with the amount of methyl formate, formic acid, and diethylene glycolic byproducts.

The amount of glycolic acid used in the selectivity calculation was calculated as the moles of formaldehyde converted minus the moles of formaldehyde equivalents in the by-products, formic acid, diglycolic acid, and methyl formate, formed.

Examples 14-20

Example 13 was repeated with the amount of methyl glycolate oligomer, aqueous formaldehyde, and triflic acid added in the amounts and at the autoclave reaction temperatures as shown in Table 8. Table 8 also gives the formaldehyde conversion along with the amount of methyl formate, formic acid, and diethylene glycolic byproducts.

TABLE 8

Batch Hydrocarboxylation with methyl glycolate oligomer scrubbed formaldehyde

| Ex. | mol of oligomer | mol of water | Triflic (wt %) | Temp | water abs. (mol %) | F0 Conv. (mol %) | G1 Selectivity (mol %) | MF (wt %) | A1 (wt %) | DG (wt %) |
|---|---|---|---|---|---|---|---|---|---|---|
| 13 | 0.19 | 0.223 | 1.32 | 120 | 43.8 | 11.5 | 94.4 | 0 | 0.01 | 0.01 |
| 14 | 0.19 | 0.209 | 2.02 | 140 | 45 | 29.4 | 91.8 | 0.09 | 0.12 | 0.09 |
| 15 | 0.19 | 0.227 | 1.32 | 140 | 44.8 | 18.7 | 89.3 | 0.09 | 0.09 | 0.01 |
| 16 | 0.21 | 0.18 | 1.99 | 160 | 46.4 | 76.8 | 97.6 | 0.13 | 0.1 | 0 |
| 17 | 0.19 | 0.223 | 1.32 | 160 | 45.3 | 58.7 | 95.1 | 0.24 | 0.25 | 0 |
| 18 | 0.16 | 0.361 | 2.01 | 160 | 42.8 | 56.5 | 91.8 | 0.91 | 0.95 | 0.02 |

TABLE 8-continued

Batch Hydrocarboxylation with methyl glycolate oligomer scrubbed formaldehyde

| Ex. | mol of oligomer | mol of water | Triflic (wt %) | Temp | water abs. (mol %) | F0 Conv. (mol %) | G1 Selectivity (mol %) | MF (wt %) | A1 (wt %) | DG (wt %) |
|---|---|---|---|---|---|---|---|---|---|---|
| 19 | 0.21 | 0.164 | 0.66 | 160 | 44.6 | 37.7 | 95.3 | 0.12 | 0.09 | 0 |
| 20 | 0.19 | 0.223 | 1.32 | 160 | 45.9 | 56.5 | 95.1 | 0.22 | 0.22 | 0 |

The following examples illustrate the continuous hydrocarboxylation of aqueous formaldehyde in methyl glycolate oligomers with triflic acid as catalyst.

Examples 21 and 22

To 13,335 g methyl glycolate oligomer made using the procedure of Example 12 with a Dp of 2.66 was added 233 grams of demineralized water, and 22.5 grams of trifluoromethanesulfonic acid in 564 grams of water. This mixture was stirred for one hour, at which point 1422 grams of 95 wt % paraformaldehyde, 5 wt % water was added in about 300 grams increments via a powder funnel. Each portion was allowed to dissolve prior to further additions (roughly one hour). The liquid mixture was maintained at a temperature of 60° C. The liquid mixture was weighed and sampled, and found to comprise 15,436 grams of material with a molar ratio of 1/1.4/1.4/0.03 moles of formaldehyde/methyl glycolate oligomer/water/triflic acid.

Example 1 was repeated using a Hastelloy 276C autoclave using the above described feed and the operating conditions given in Table 9. The pressure was let down and the reactor effluent collected for analysis via high pressure liquid chromatography. The molar ratios of methyl glycolate oligomer/water/formaldehyde/triflic acid for each experimental point are given in Table 9. Also summarized in Table 9, are feed flow rates, reactor temperature, pressure, and residence time for each experimental point.

Conversion, space-time yield, and selectivity of reacted formaldehyde to end products are summarized in Table 10. Calculations of conversion, space-time yield, and selectivity were based only on fresh formaldehyde feed and did not include glycolic acid already present in the feed mixture. Process temperature, pressure, feed flow rate, and feed composition were maintained constant for 24 to 72 hours. Each point represents the average analysis at each set of conditions. The feed was kept at 60° C. throughout the reaction period to ensure no solid formaldehyde precipitated.

During analysis, glycolic acid oligomers and other forms of glycolic acid were hydrolyzed and converted to free monomeric glycolic acid equivalents. The selectivity of formaldehyde to glycolic acid is reported based upon free glycolic acid equivalents. Methanol was present as both free methanol and methyl glycolate, and was converted to free methanol and glycolic acid by the analytical method.

Conversion is defined as the moles of formaldehyde (as paraformaldehyde) reacted divided by moles of formaldehyde fed. Molar selectivity is defined as the moles of each hydrocarboxylation reaction product species created per mole of formaldehyde reacted. Selectivity calculations do not include unreacted formaldehyde.

TABLE 9

Feed Rates, Feed Ratios, and Reaction Conditions

| Example | Feed Rate g/min | F0 | $H_2O$ | MG Oligomer | Triflic | Temp. Celsius | Pressure Bara | Residence Time minutes |
|---|---|---|---|---|---|---|---|---|
| 21 | 0.98 | 1.0 | 1.4 | 1.4 | 0.030 | 170 | 83.8 | 90 |
| 22 | 0.98 | 1.0 | 1.4 | 1.4 | 0.030 | 180 | 83.8 | 90 |

TABLE 10

Molar Selectivity, Conversion, and Space-Time Yield Results

| Ex. | F0 Conv. | G1 | A1 | MeOH | MGH | DG | STY mol/liter/hr |
|---|---|---|---|---|---|---|---|
| 21 | 72% | 82.00% | 0.90% | 0.00% | 20.00% | 0% | 1.8 |
| 22 | 80% | 65.00% | 0.08% | 0.00% | 33.00% | 0% | 2.0 |

The following examples illustrate the effect of glycolic acid oligomers on conversion and selectivity in the hydrocarboxylation of aqueous formaldehyde.

Examples 23-26

Example 1 was repeated with the feed rate and compositions shown in Table 11. The feed molar ratios, pressure, temperature, and residence time are given in Table 12. In example 23, paraformaldehyde, water, sulfuric acid, and monomeric glycolic acid were mixed to form the feed material. In Examples 23-26, monomeric glycolic acid was first subjected to oligomerization as follows. Monomeric glycolic acid was melted in a round-bottom flask fitted with a take-off head, condenser, overhead paddle stirrer, nitrogen purge, and electrical heating mantle. Water was removed under vacuum (about 0.13 bara) until the average degree of polymerization was about 2.6. The glycolic acid oligomer was then mixed with water, paraformaldehyde, and sulfuric acid to give the feed composition for Examples 23-26 specified in Tables 11 and 12. Conversion, space-time yield, and selectivity of reacted formaldehyde to end products are summarized in Table 13. During analysis, glycolic acid oligomers and other forms of glycolic acid were hydrolyzed and converted to free monomeric glycolic acid equivalents. The selectivity of formaldehyde to glycolic acid is reported based upon free glycolic acid equivalents. Methanol was present as both free methanol and methyl glycolate, and was converted to free methanol and glycolic acid by the analytical method.

TABLE 11

Feed 1: Rate and Composition

| Ex | g/min | Paraformaldehyde | Water | G1 | $H_2SO_4$ |
|---|---|---|---|---|---|
| 23 | 1.25 | 13.0 | 17.2 | 66.0 | 3.8 |
| 24 | 1.25 | 14.1 | 20.9 | 61.1* | 3.8 |
| 25 | 1.25 | 14.1 | 20.9 | 61.1* | 3.8 |
| 26 | 1.25 | 14.1 | 20.9 | 61.1* | 3.8 |

*as glycolic acid oligomers with an average degree of polymerization of about 2.6

TABLE 12

Overall Feed Ratios and Reaction Conditions

| | Feed Molar Ratio | | | | Temp | Press | Res Time |
|---|---|---|---|---|---|---|---|
| Ex | Paraformaldehyde | water | G1 | $H_2SO_4$ | Celsius | bara | minutes |
| 23 | 1.0 | 2.2 | 2.0 | 0.089 | 205 | 180 | 55 |
| 24 | 1.0 | 2.47 | 2.0* | 0.083 | 205 | 180 | 55 |
| 25 | 1.0 | 2.47 | 2.0* | 0.083 | 205 | 180 | 55 |
| 26 | 1.0 | 2.47 | 2.0* | 0.083 | 205 | 180 | 55 |

*as glycolic acid oligomers with an average degree of polymerization of about 2.6

TABLE 13

Selectivity, Conversion, and Space-Time Yield Results

| | % FO Conv | Molar Selectivity | | | | | Space-Time Yield |
|---|---|---|---|---|---|---|---|
| Ex | | G1 | A1 | DG | MGH | MeOH | gmol/l-hr |
| 23 | 93.5 | 89.0 | 2.8 | 4.3 | 2.5 | 1.5 | 3.52 |
| 24 | 95.5 | 91.2 | 1.4 | 4.6 | 2.6 | 0.2 | 3.88 |
| 25 | 95.5 | 91.8 | 1.3 | 4.5 | 2.2 | 0.2 | 4.16 |
| 26 | 95.4 | 91.7 | 1.3 | 4.6 | 2.4 | 0.1 | 4.15 |

We claim:

1. A process for the preparation of glycolic acid, comprising
   (A) feeding carbon monoxide, aqueous formaldehyde, and a recycle dehydration stream to a hydrocarboxylation reaction zone to produce an effluent comprising glycolic acid, glycolic acid oligomers, and water;
   (B) dehydrating said effluent to produce a first dehydration stream having a higher degree of polymerization (Dp) than said effluent and a water stream; and
   (C) splitting said first dehydration stream into said recycle dehydration stream of step (A) and an intermediate stream,
   wherein said feeding of said recycle dehydration stream and said aqueous formaldehyde of step (A) occurs at a molar ratio of ester bond equivalents:water of from 0.2:1 to 4:1.

2. The process according to claim 1, wherein said first dehydration stream comprises glycolic acid and glycolic acid oligomers having said degree of polymerization (Dp) of from 1.1 to 4.0.

3. The process according to claim 1, wherein said first dehydration stream comprises glycolic acid and glycolic acid oligomers having said degree of polymerization (Dp) of from 1.5 to 3.0.

4. The process according to claim 1, wherein said feeding of said recycle dehydration stream and said aqueous formaldehyde of step (A) occurs at a molar ratio of ester bond equivalents:water of from 1.0:1 to 2.5:1.

5. The process according to claim 1, wherein said aqueous formaldehyde comprises 35 weight percent to 85 weight percent formaldehyde, based on the total weight of said aqueous formaldehyde, the molar ratio of carbon monoxide to formaldehyde ranges from 1:1 to 10:1, and said hydrocarboxylation reaction zone is operated at a pressure of from 35 bar gauge to 200 bar gauge and a temperature of from 80° C. to 220° C.

6. The process according to claim 5, wherein said hydrocarboxylation zone is operated at said temperature of from 160° C. to 210° C.

7. The process according to claim 1, wherein said aqueous formaldehyde and said recycle dehydration stream are contacted and allowed to react prior to said feeding of step (A).

8. The process according to claim 1, further comprising
   (D) reacting said intermediate stream with a first ethylene glycol while simultaneously removing water to produce an esterification effluent comprising EG glycolate ester oligomers and glycolic acid oligomers and an overhead stream comprising water; and
   (E) reacting hydrogen with said esterification effluent to produce a second ethylene glycol, separating said second ethylene glycol into a product ethylene glycol and said first ethylene glycol, and recycling said first ethylene glycol to step (D).

9. A process for the preparation of glycolic acid, comprising
   (A) feeding carbon monoxide, aqueous formaldehyde, and a recycle dehydration stream to a hydrocarboxylation reaction zone to produce an effluent comprising glycolic acid, glycolic acid oligomers, methyl glycolate, methyl glycolate oligomers, and water;
   (B) dehydrating said effluent in the presence of methanol to produce a first dehydration stream having a degree of polymerization (Dp) higher than said effluent and an overhead stream comprising water and methanol; and
   (C) splitting said first dehydration stream into said recycle dehydration stream of step (A) and an intermediate stream,
   wherein said feeding of said recycle dehydration stream and said aqueous formaldehyde of step (A) occurs at a molar ratio of ester bond equivalents:water of from 0.2:1 to 4:1.

10. The process according to claim 9, wherein said first dehydration stream comprises glycolic acid, glycolic acid oligomers, methyl glycolate, and methyl glycolate oligomers having said degree of polymerization (Dp) of from 1.1 to 4.0.

11. The process according to claim 9, wherein said first dehydration stream comprises glycolic acid, glycolic acid oligomers, methyl glycolate, and methyl glycolate oligomers having said degree of polymerization (Dp) of from 1.5 to 3.0.

12. The process according to claim 9, wherein said feeding of said recycle dehydration stream and said aqueous formaldehyde of step (A) occurs at a molar ratio of ester bond equivalents:water of from 1.0:1 to 2.5:1.

13. The process according to claim 9, wherein said aqueous formaldehyde comprises 35 weight percent to 85 weight percent formaldehyde, based on the total weight of said aqueous formaldehyde, the molar ratio of carbon monoxide to formaldehyde ranges from 1:1 to 10:1, and said hydrocarboxylation reaction zone is operated at a pressure of from 35 bar gauge to 200 bar gauge and a temperature of from 80° C. to 220° C.

14. The process according to claim 13, wherein said hydrocarboxylation reaction zone is operated at said temperature of from 160° C. to 210° C.

15. The process according to claim 9, wherein said aqueous formaldehyde and said recycle dehydration stream are contacted and allowed to react prior to said feeding of step (A).

16. The process according to claim 9, further comprising (D) hydrogenating said intermediate stream to produce ethylene glycol.

17. The process according to claim 9, further comprising
- (D) reacting said intermediate stream with a first ethylene glycol while simultaneously removing water and methanol to produce an esterification effluent comprising EG glycolate ester oligomers and glycolic acid oligomers and an overhead stream comprising water and methanol; and
- (E) reacting hydrogen with said esterification effluent to produce a second ethylene glycol, separating said second ethylene glycol into a product ethylene glycol and said first ethylene glycol, and recycling said first ethylene glycol to step (D).

* * * * *